United States Patent [19]

Flaim et al.

[11] Patent Number: 5,726,209
[45] Date of Patent: Mar. 10, 1998

[54] LIQUID FLUOROCARBON EMULSION AS A VASCULAR NITRIC OXIDE RESERVOIR

[75] Inventors: Stephen F. Flaim, San Diego, Calif.; Jean G. Riess, Nice, France

[73] Assignee: Alliance Pharmaceutical Corp., San Diego, Calif.

[21] Appl. No.: 501,976

[22] Filed: Jun. 7, 1995

[51] Int. Cl.$^6$ ............................ A61K 31/02; A61K 33/00
[52] U.S. Cl. ........................ 514/761; 514/759; 424/718
[58] Field of Search ............................ 514/761, 759; 424/718

[56] References Cited

U.S. PATENT DOCUMENTS

| | | |
|---|---|---|
| 4,781,676 | 11/1988 | Schweighardt et al. |
| 4,865,836 | 9/1989 | Long |
| 4,866,096 | 9/1989 | Schweighardt |
| 4,895,876 | 1/1990 | Schweighardt et al. |
| 4,927,623 | 5/1990 | Long |
| 4,987,154 | 1/1991 | Long |
| 4,993,415 | 2/1991 | Long |

FOREIGN PATENT DOCUMENTS

| | | |
|---|---|---|
| WO9302653 | 2/1993 | WIPO |
| WO9400180 | 1/1994 | WIPO |
| 9409625 | 5/1994 | WIPO |
| 9510267 | 4/1995 | WIPO |
| 9512394 | 5/1995 | WIPO |

OTHER PUBLICATIONS

Buddemeier, et al. "Oxygent® (Oxygen–Carrying Perfluorochemical Emulsion) Preserves Endothelial Dependent and Independent Vasodilator Responses After Experimental Myocardial Infarction and Reperfusion" Clinical Research Meeting Apr. 29–May 2, 1994.

Carter, et al. "Nitric Oxide Production is Intensely and Persistently Increased in Tissue by Thermal Injury" Biochem. J. 304: 201–204 (1994).

Kovach, et al. "Endothelial Dysfunction in Shock States" Am. Physiol. Soc. 8: 145–148 (1993).

Kovach, et al. "Effects of $N^G$–Nitro–L–Arginine and L–Arginine on Regional Cerebral Blood Flow in the Cat" J. of Physiology 449: 183–196 (1992).

Lefer, et al. "Microvascular Actions of Nitric Oxide Donors in Circulatory Disorders" *Nitric Oxide Conference*, Mar. 27–28, 1995 (8 pgs.).

Lefer, et al. "Antineutrophil and Myocardial Protecting Actions of a Novel Nitric Oxide Donor After Acute Myocardial Ischemia and Reperfusion in Dogs" Circulation 88(5 Part 1): 2337–2350 (1993).

Milner, Anthony D. "Nitric Oxide" Eur. J. Pediatr. 153 (Suppl 2): S7–S11 (1994).

"Inhaled Nitric Oxide for the Adult Respiratory Distress Syndrome" New England J. of Medicine 329(3): 206–207 (1993).

Pinsky, et al. "The Role of Nitric Oxide in Cardiac Preservation for Transplantation" Circulation 88(4 Part 2): (1993).

Roberts, et al. "Inhaled Nitric Oxide in Persistent Pulmonary Hypertension of the Newborn" The Lancet 340:818–819 (1992).

Rubanyi, Gabor M. "The Role of Endothelium in Cardiovascular Homeostasis and Diseases" J. of Cardiovascular Pharmacology 22 (Suppl 4): S1–S14 (1993).

Rubanyi, et al. "Cytoprotective Function of Nitric Oxide: Inactivation of Superoxide Radicals Produced by Human Leukocytes" Biochem. and Biophys. Res. Commun. 181(3): 1392–1397 (1991).

Suzuki, et al. "Hemoglobin Augmentation of Interleukin-1β–Induced Production of Nitric Oxide in Smooth–Muscle Cells" J. Neurosurg 81: 895–901 (1994).

"Perfluorochemical Blood Substitutes" *Technical Information Ser. No. 5* (pp. 1–177) Jun. 30, 1978.

"Perfluorochemical Blood Substitutes" *Technical Information Ser. No. 7* (pp. 1–119) Jul. 30, 1981.

Kinsella, et al. "Clinical Responses to Prolonged Treatment of Persistent Pulmonary Hypertension of the Newborn with Low Doses of Inhaled Nitric Oxide" J. of Pediatrics 123(1): 103–108 (1993).

Zayek, et al. "Treatment of Persistent Pulmonary Hypertension in the Newborn Lamb by Inhaled Nitric Oxide:" J. of Pediatrics 122(5 Part 1): 743–750 (1993).

Fazekas, et al. "Effect of Nitric Oxide Inhibition on Capsaicin–Elicited Vasodilation in the Rat Oral Circulation" Res. Esp. Med. 194: 357–365 (1994).

Leach et al, *Pediatric Research*, vol. 35, No. 4 Part 2, Apr. 1994, p. 394A, abstract No. 2351.

*Primary Examiner*—William R. A. Jarvis
*Attorney, Agent, or Firm*—Knobb, Martens, Olson & Bear, LLP.

[57] ABSTRACT

Biocompatible fluorocarbon emulsions are utilized to inhibit the removal of endogenously produced nitric oxide from the bloodstream, and to thereby inhibit vascular stenosis, vasoconstriction, and any other physiological condition or disorder arising in whole or in part from a deficiency of endogenous nitric oxide.

14 Claims, 1 Drawing Sheet

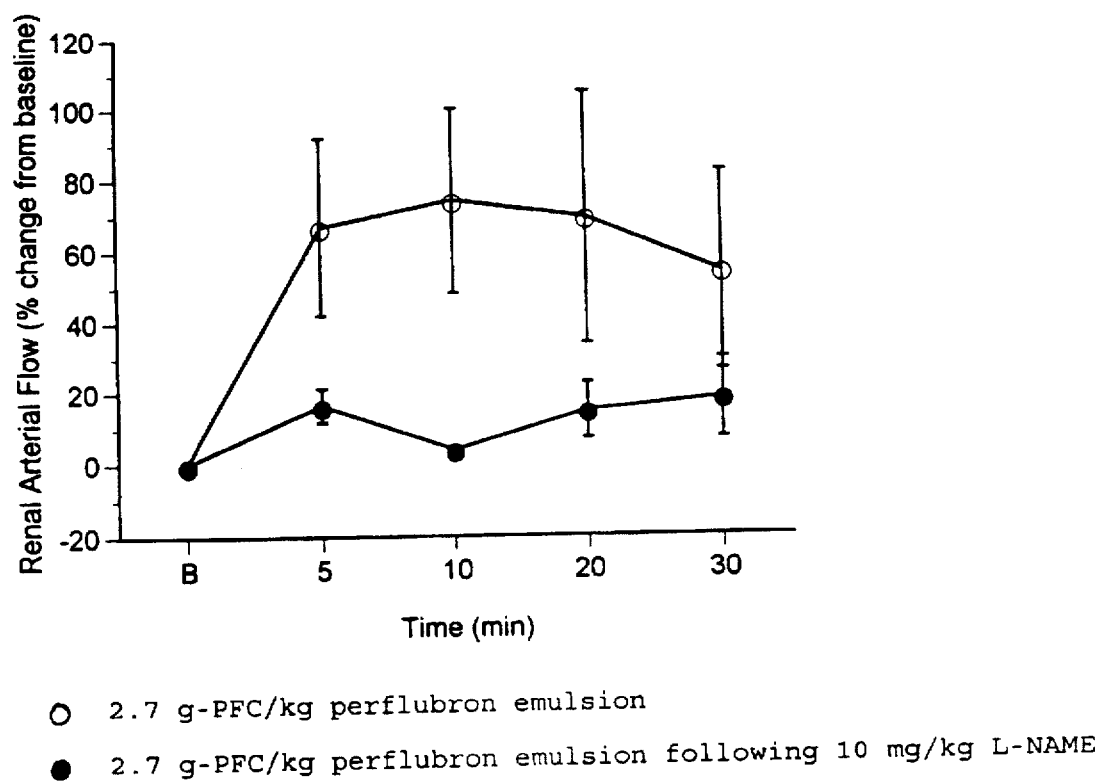

LIQUID FLUOROCARBON EMULSION AS A VASCULAR NITRIC OXIDE RESERVOIR

FIELD OF THE INVENTION

The present invention relates to the use of liquid fluorocarbon emulsions to treat local or systemic disease conditions resulting at least in part from a deficiency in endogenous nitric oxide.

BACKGROUND OF THE ART

Endogenous nitric oxide is key in the maintenance of microcirculatory homeostasis. It is formed biologically by the oxidation of L-arginine by nitric oxide synthases. Among other functions, nitric oxide is known to inhibit thrombogenicity, regulate immunity, serve as a neurotransmitter, and to participate in wound healing. For example, dramatic increases in levels of urinary nitrate excretion and nitric oxide synthase activity in tissues has been observed following non-lethal burn injuries. *Biochemical Journal* (United Kingdom) 304/1 pp 201–204 (1994).

Nitric oxide is also an effective vasodilator, and its absence locally or systemically is associated with vasoconstriction. It is known to be secreted by vascular endothelial cells, and when released into the underlying vascular wall, is able to induce relaxation of smooth muscle cells, thereby causing subsequent vasodilation. Nitric oxide formation has been shown to play a significant role in vasodilation induced by capsaicin administration in rat oral tissue structures such as the gingiva, tongue, and submandibular glands. *Research in Experimental Medicine* 194/6 pp 357–365 (1994). Furthermore, pulmonary administration of nitric oxide has been proposed as an alternative to various vasodilators such as tolazoline, prostacyclin, and nitroprusside in the treatment of pulmonary hypertension and respiratory distress syndrome in newborns. *European Journal of Pediatrics* 153/9 Suppl. 2 pp S7-S11 (1994).

Nitric oxide which is released from the vascular endothelium into the adjacent blood plasma, however, is rapidly scavenged by plasma hemoglobin. The plasma half life of nitric oxide is therefore limited to several seconds. This continuous loss of nitric oxide to the plasma adjacent to the vascular endothelium can limit the effectiveness of endogenously produced nitric oxide.

In addition to limiting the effectiveness of locally produced endogenous nitric oxide, this low plasma persistence renders exogenous nitric oxide an organ specific pulmonary vasodilator. This is because nitric oxide introduced into the respiratory tract (by breathing an atmosphere supplemented with nitric oxide gas) is removed from circulation by hemoglobin passing through the pulmonary arteries. Consequently, only the vasculature of the lung is affected by this route of nitric oxide administration, and nitric oxide therapies have so far been limited to treating lung disorders.

In addition to the removal of plasma-dissolved nitric oxide, the scavenging of nitric oxide by hemoglobin has another significant result. Nitric oxide which has bonded to hemoglobin is known to deactivate hemoglobin by forming methemoglobin. Although hemoglobin inside red blood cells is protected from such deactivation by intracellular enzyme systems, extracellular hemoglobin in the surrounding plasma is subject to deactivation by endogenous nitric oxide. Although the plasma half life of nitric oxide is short, its presence can still inhibit the effectiveness of therapies involving the administration of exogenous hemoglobin which is exterior to the red blood cells. This is a particularly important problem for liposome encapsulated hemoglobin products.

A need therefore exists to regulate the presence of plasma-dissolved nitric oxide. First, local or systemic disease conditions which result at least in part from a deficiency in endogenous nitric oxide may be alleviated by extending the circulating plasma lifetime of nitric oxide and thereby maximizing the diffusion of nitric oxide into the vascular wall throughout the circulatory system. In addition, therapies which involve the administration of exogenous hemoglobin may be improved by reducing the availability of met-hemoglobin forming plasma-dissolved nitric oxide.

SUMMARY OF THE INVENTION

The present invention utilizes biocompatible fluorocarbon emulsions to enhance the beneficial effects of endogenously produced nitric oxide, and also the improve the efficacy of therapies involving the administration of exogenous nitric oxide. Although fluorocarbon emulsions have been used as oxygen carrying and delivery agents, their efficacy as nitric oxide carriers has not before been recognized or utilized in treatment protocols.

The relatively high solubility of gases in liquid fluorocarbon allows the discontinuous phase of an intravenously injected fluorocarbon emulsion to function as a nitric oxide reservoir. The droplets of liquid fluorocarbon provide a segregated space into which plasma dissolved nitric oxide can diffuse and remain protected from contact with plasma hemoglobin.

Accordingly, a method for increasing the amount of nitric oxide circulating in the bloodstream of a patient in need of increased circulating nitric oxide is disclosed, which comprises the intravenous administration of an effective amount of a liquid fluorocarbon emulsion. Circulating nitric oxide levels may be further enhanced by the pulmonary administration of an effective amount of exogenous nitric oxide, or by dissolving an effective amount of nitric oxide in the fluorocarbon prior to intravenous administration of the fluorocarbon emulsion. Physiological conditions which may be more effectively treated utilizing the methods of the present invention include vasospasm and vascular stenosis. Nitric oxide promotion will also attenuate increased peripheral vascular resistance.

It is a further aspect of the present invention that treatments involving the administration of exogenous hemoglobin may be improved by the concurrent administration of liquid fluorocarbon emulsions. Concurrent fluorocarbon administration will reduce the availability of free nitric oxide in the plasma, thereby reducing nitric oxide-induced hemoglobin deactivation.

BRIEF DESCRIPTION OF THE FIGURE

The figure is a graph of the measurement of renal blood flow in rabbits which were injected with a fluorocarbon emulsion as compared with rabbits injected with both a fluorocarbon emulsion and L-NAME, an inhibitor of nitric oxide production.

DETAILED DESCRIPTION OF THE INVENTION

Fluorocarbon emulsions find uses as both therapeutic and diagnostic agents. Because fluorocarbon liquids are known to dissolve high concentrations of gases such as oxygen and carbon dioxide, most therapeutic applications of fluorocarbons are related to their oxygen carrying capacity. Both pure liquid fluorocarbon and aqueous fluorocarbon emulsions have therefore been successfully utilized as oxygen delivery agents. One commercially available fluorocarbon emulsion, Fluosol (Green Cross Corp., Osaka, Japan) may be used as a gas carrier to oxygenate the myocardium during percutaneous transluminal coronary angioplasty (R. Naito, K. Yokoyama, Technical Information Series No. 5 and 7, 1981). In addition, cancer therapies have been developed which involve the delivery of oxygen to tumor tissue via a fluorocarbon carrier. The inhalation of an oxygen enriched atmosphere prior to or concurrently with the intravenous injection of fluorocarbon emulsion has been utilized to maximize radiation therapy of cancers. U.S. Pat. No. 4,781,676 to Schweighardt, et al. discloses the injection of oxygenated fluorocarbon emulsion directly into tumor cells in order to improve the effectiveness of radiation therapy on the hypoxic regions of the tumor mass.

The oxygen carrying capacity of liquid fluorocarbons has also led to their use as blood substitutes, and in partial liquid ventilation applications, wherein a subject animal or patient breathes oxygenated liquid fluorocarbon to deliver oxygen through the lungs to the bloodstream. Fluorocarbon emulsions have also been used in diagnostic imaging applications. Radiopaque fluorocarbon such as perfluorooctyl bromide ($C_8F_{17}Br$, "PFOB" or "perflubron") are useful for this purpose, with 1-bromoperfluorooctane being particularly prefered.

Although there have been no models developed to accurately predict the solubilities of gases in liquid fluorocarbon, the solubilities of gases generally increase with increasing molecular volume. Nitric oxide, therefore, should have a liquid fluorocarbon solubility intermediate between molecular oxygen ($O_2$) and molecular nitrogen ($N_2$). Based on molecular volume, the solubility of $O_2$ may be estimated to be approximately 20 mM at 37 degrees C., while the solubility of $N_2$ may be estimated to be approximately 14 mM. Nitric oxide, therefore, is likely to have a solubility of approximately 17 mM at 37 degrees C., which corresponds to approximately 38% v/v of a fluorocarbon/nitric oxide mixture.

The ability of liquid fluorocarbon to deliver clinically significant amounts of nitric oxide to the respiratory tract has been demonstrated in animal studies. In one such study, pulmonary hypertension was induced in six lambs by intravenous administration of U46619 (2 mcg/kg/min). The animals were both conventionally ventilated with an atmosphere containing up to 80 ppm nitric oxide, and ventilated via partial liquid ventilation using nitric oxide containing liquid fluorocarbon. In both cases, decreased pulmonary artery pressure and vascular resistance were observed. No difference in nitric oxide pharmacokinetics was noted between nitric oxide administered conventionally, or administered dissolved in liquid fluorocarbon.

As was mentioned above, however, the problem remains that the clinical effects of the nitric oxide therapy are limited to lung tissue. The present invention provides a method for promoting high plasma nitric oxide levels in a subject in need of increased nitric oxide concentration at a location in the body other than the vasculature of the lung.

The rate of removal of free nitric oxide from circulating blood plasma would be reduced if the nitric oxide was segregated from the hemoglobin also present. The relatively high solubility of gases in liquid fluorocarbon allows the discontinuous phase of an intravenously injected fluorocarbon emulsion to perform this function. The droplets of liquid fluorocarbon provide a segregated space into which plasma-dissolved nitric oxide can diffuse and remain protected from contact with plasma hemoglobin. Further increases in nitric oxide delivery to remote tissues and organs may be achieved by dissolving nitric oxide in the fluorocarbon prior to injection, rather than injecting a nitric oxide free fluorocarbon emulsion, and having endogenous nitric oxide diffuse from the plasma into the emulsion droplets. Nitric oxide therapies are therefore enhanced by the concurrent use of intravenously injected fluorocarbon emulsions.

A fluorocarbon emulsion comprises a continuous aqueous phase, and a discontinuous liquid fluorocarbon phase. Methods of creating biocompatible fluorocarbon emulsions suitable for intravenous injection into an animal or human are known to those in the art. Although fluorocarbon particle size is not particularly crucial when an emulsion is used in non-venous systems in the body such as the cerebrospinal fluid ventricles and cavities, for intravenous use, it is preferable to have small particle size, preferably about 0.05 to 0.3 microns. Larger particle sizes are dangerous in that they tend to collect in the liver, spleen, lung, and some other organs, enlarging them and endangering their function.

Typically, the emulsion is stabilized with an emulsifying agent. Osmotic agents and biocompatible pH buffers are also generally included in the aqueous phase to maintain biologically suitable osmolarity and pH. Maintaining normal osmolarity of between approximately 290 to 300 milliosmols may help prevent injury to cells such as red blood cells and vascular endothelial cells which the emulsion contacts upon injection. However, in some applications, notably oxygenation during cardio-pulmonary bypass, it has been found that emulsion performance is improved by providing a solution of higher osmolarity, preferably approximately 700 or 800 milliosmols. This aspect of fluorocarbon emulsion use is described in U.S. Pat. No. 5,114,932 to Runge, the disclosure of which is hereby incorporated by reference.

A large number of various commercially available fluorocarbons and fluorocarbon combinations are known to make suitable emulsions. Monobrominated fluorocarbons such as perfluorooctylbromide ($C_8F_{17}Br$, "PFOB" or "perflubron"), 1-bromopentadecafluoroseptane ($C_7F_{15}Br$), and 1-bromotridecafluorohexane ($C_6F_{13}Br$, perfluorohexylbromide, or "PFHB") are known to make suitable emulsions and are also known to have high oxygen solubility. Preferably, the fluorocarbon is present in the aqueous phase at approximately 5–125% weight in grams to emulsion volume in milliliters.

The emulsifying agent may comprise a surfactant such as lecithin, a polyoxyethylene-polyoxypropylene copolymer, or a fatty acid. Fluorinated surfactants have also been found suitable. The ingredients described above are emulsified using techniques known in the art, for example, by high pressure homogenization in a commercially available microfluidizer.

The osmotic agent may be a hexa-hydric alcohol such as mannitol or sorbitol, or a sugar such as glucose, mannose or fructose. Osmolarity is also affected by buffers, which may be selected from imidazole or tris-hydroxymethyl-aminomethane (both of which are beneficial in that they do not precipitate calcium) or may also be selected from such buffering agents as sodium chloride, sodium bicarbonate, magnesium chloride, mono- or dibasic potassium phosphate, calcium chloride, magnesium sulfate, or mono- or dibasic sodium bicarbonate. Biocompatible combinations of these agents provide for the reduction of red blood cell injury in vivo and in vitro, for reduction in viscosity, and for reduction in the rate of oxidation.

Those liquid fluorocarbon emulsions having efficacy as oxygen carriers should also have sufficient nitric oxide solubility to be efficacious in terms of the promotion of plasma-dissolved nitric oxide. Consequently, fluorocarbon emulsions in accordance with the present invention should be prepared to have suitable properties in terms of shelf life, biocompatibility, and particle size stability. Descriptions of some methods of preparing biocompatible fluorocarbon emulsions suitable for use with the present invention are described in U.S. Pat. No. 4,895,876 to Schweighardt et al., U.S. Pat. No. 4,866,096 to Schweighardt, in U.S. Pat. Nos. 4,865,836, 4,993,415, 4,987,154, and 4,927,623 to Long, and International Application Number PCT/US93/10286 (International Publication Number WO 94/09625) to Weers, et al., the disclosures of which are hereby incorporated by reference.

Thus, in one embodiment of the present invention, a patient in need of vasodilation is given an intravenous dose of an effective nitric oxide-sequestering amount of fluorocarbon emulsion. The effect is expected to persist for approximately the half-life of the emulsion in circulation, which is known to vary with different fluorocarbons and fluorocarbon mixtures, but which is on the order of hours to days. Repeat doses are also contemplated.

As was described above, the nitric oxide sequestering function is also useful in conjunction with hemoglobin therapies. In this embodiment of the invention, a patient receiving exogenous hemoglobin receives an effective, hemoglobin-protecting amount of fluorocarbon emulsion prior to, concurrent with, or soon after administration of the hemoglobin.

In yet another embodiment of the invention, a patient suffering from any other physiological condition arising in whole or in part from a deficiency of endogenous nitric oxide is given an effective nitric oxide sequestering amount of intravenous fluorocarbon emulsion. Physiological conditions which may be treated with such therapy include circulatory shock, artherosclerosis, and restenosis following vascular injury.

In any of these treatments, the amount of fluorocarbon emulsion administered is generally between about 0.5 and 5.0 g-PFC/kg, more preferably from about 1.0, 1.2, or 1.4 g-PFC/kg to about 1.6, 2.0, or 3.0 g-PFC/kg, expressed as the total weight in grams of administered fluorocarbon in the emulsion per kilogram of body weight. Because the physiological changes, most particularly the hemodynamic changes, associated with fluorocarbon emulsion administration are relatively easily measured, the optimum dosage for any particular disease or condition can be determined without undue experimentation by determining the dose/response relationship for a particular fluorocarbon in that patient.

Some therapies would be further enhanced by the inclusion of exogenous nitric oxide into the emulsion prior to injection. To accomplish this, methods known in the art for dissolving gas into the discontinuous phase of fluorocarbon emulsions may be employed. Due to the use of fluorocarbon emulsions as oxygen delivery agents, these techniques have previously been applied to fluorocarbon oxygenation. In the simplest embodiment, one merely contacts the gas and the liquid fluorocarbon. Blood oxygenators and the like are examples of suitable commercially available equipment. In one exemplary procedure, the emulsion is placed in a flexible bag with the gas to be dissolved into the fluorocarbon. This method takes advantage of the fact that the fluorocarbon and fluorocarbon emulsions tend to form a film or layer on the inner surface of the flexible container because of the low surface tension of the emulsion. Preferably, the emulsion fills less than half of the bag when the bag is inflated with gas. After inflation with the appropriate gas, the bag is moved around and rotated so that the emulsion coats the inside surface of the bag in a film. The gas then easily dissolves into the fluorocarbon discontinuous phase. This and other methods of gas dissolution are described in detail in U.S. Pat. No. 4,927,623 to Long, incorporated herein by reference. In accordance with the present invention, the gas is preferably nitrogen mixed with an effective amount of nitric oxide. The concentration of nitric oxide in the gas to be dissolved may be widely varied, from near zero to 50, 80, or 100 ppm or higher.

Nitric oxide may also be delivered to the emulsion in vivo, by exposing the subject to an atmosphere containing nitric oxide after or concurrent with the intravenous injection of a biocompatible emulsion as described above. The concentration of nitric oxide in the inhaled gas may also be varied widely. This method of nitric oxide administration has been shown to be effective at concentrations of less than 5 ppm. Preferably, the inhaled gas will be 20 to 150 ppm nitric oxide. Therapies involving the inhalation of exogenous nitric oxide are well known in the art. Some are described in more detail in Lancet 340:818–819 (1992), J. Pediatrics 122:743–750 (1993), J. Pediatrics 123:103–108 (1993), and N. Eng. J. Med. 329:207 (1993), the disclosures of which are hereby incorporated by reference.

In this embodiment of the present invention, the amount of fluorocarbon emulsion administered is also generally between about 0.5 and 5.0 g-PFC/kg, more preferably from about 1.0, 1.2, or 1.4 g-PFC/kg to about 1.6, 2.0, or 3.0 g-PFC/kg, expressed as the total weight in grams of administered fluorocarbon in the emulsion per kilogram of body weight. Once again, the optimum dosage for any particular disease or condition can be determined without undue experimentation by determining the dose/response relationship for a particular fluorocarbon in that patient.

It may be emphasized, however, that the benefits of liquid fluorocarbon emulsion as a nitric oxide reservoir are not limited to therapies which involve the administration of exogenous nitric oxide. The fluorocarbon droplets in the bloodstream provide a protected space into which nitric oxide in the plasma will diffuse, thereby promoting nitric oxide levels in the bloodstream, especially in those tissues where the fluorocarbon tends to collect. It may also be noted that fluorocarbon emulsion administration associated with the introduction of exogenous hemoglobin is preferably performed without additional nitric oxide either in the fluorocarbon or introduced into the respiratory tract.

EXAMPLE

Increase in Rabbit Renal Blood Flow Following Perflubron Emulsion Injection

Seven rabbits were anesthetized and a doppler flow measurement device was installed on the renal artery. After an appropriate period of stabilization and continued anesthesia, rabbits were injected intravenously with 2.7 g-PFC/kg 90% w/v perflubron emulsion stabilized with egg yolk phospholipid (type AF0104, Alliance Pharmaceutical, San Diego, Calif.) while monitoring renal vasodilation effects. Subsequently, after renal flow returned to baseline, three of the rabbits were injected with 10 mg/kg L-NAME, an inhibitor of endothelial nitric oxide production. All seven rabbits were then again injected intravenously with the 2.7 g-PFC/kg perflubron emulsion (type AF0104, Alliance Pharmaceutical, San Diego, Calif.) while monitoring renal vasodilation effects.

The figure illustrates the response of the rabbit renal blood flow to this second intravenous administration of liquid fluorocarbon emulsion. As can be seen in the Figure, emulsion alone produced a 60% increase in renal blood flow within 5 minutes and persisted for over 30 minutes. In contrast, the prior injection of L-NAME ($N^G$-nitro-L-arginine methyl ester), a nitric oxide synthase inhibitor, reduced or eliminated the blood flow increase. This indicates sufficient fluorocarbon uptake of endogenous nitric oxide to increase nitric oxide stable half-life in the plasma, and thereby enhance nitric oxide induced renal vasodilation.

The foregoing description details certain preferred embodiments of the present invention and describes the best mode contemplated. It will be appreciated, however, that no matter how detailed the foregoing appears in text, the invention can be practiced in many ways and the invention should be construed in accordance with the appended Claims and any equivalents thereof.

What is claimed:

1. A method for increasing the amount and the stable half-life of nitric oxide circulating in the bloodstream of a patient in need of an increase in the amount and stable half-life of circulating nitric oxide comprising the intravenous administration of an effective amount of a liquid fluorocarbon emulsion.

2. The method of claim 1 additionally comprising the step of pulmonary administration of an effective amount of exogenous nitric oxide.

3. The method of claim 1 additionally comprising the step of dissolving an effective amount of nitric oxide in the fluorocarbon prior to intravenous administration of the fluorocarbon emulsion.

4. The method of claim 1 wherein the fluorocarbon in the emulsion comprises perfluorooctylbromide.

5. The method of claim 1 wherein the patient is a human.

6. A method for treating conditions resulting in whole or in part from a deficiency in endogenous nitric oxide comprising the intravenous administration of an effective amount of a fluorocarbon emulsion prior to or concurrent with the pulmonary administration of an effective amount of exogenous nitric oxide.

7. A method for promoting nitric oxide induced vasodilation comprising intravenous administration to a patient in need of vasodilation an effective nitric oxide sequestering amount of a fluorocarbon emulsion, wherein said fluorocarbon emulsion provides an increase in the amount and stable half-life of circulating nitric oxide.

8. The method of claim 7 additionally comprising the step of pulmonary administration of an effective amount of exogenous nitric oxide.

9. The method of claim 7 additionally comprising the step of dissolving an effective amount of nitric oxide in the fluorocarbon prior to intravenous administration of the fluorocarbon emulsion.

10. The method of claim 1 wherein said patient suffers from a condition selected from the group consisting of circulatory shock, atherosclerosis, vasospasm, vascular stenosis and increased peripheral vascular resistance.

11. The method of claim 1 wherein said patient suffers from cancer.

12. The method of claim 6 wherein said patient suffers from a condition selected from the group consisting of circulatory shock, atherosclerosis, vasospasm, vascular stenosis and increased peripheral vascular resistance.

13. The method of claim 7 wherein said patient suffers from a condition selected from the group consisting of circulatory shock, atherosclerosis, vasospasm, vascular stenosis and increased peripheral vascular resistance.

14. The method of claim 7 wherein said patient suffers from cancer.

* * * * *